US009005169B2

(12) United States Patent
Gravesen et al.

(10) Patent No.: US 9,005,169 B2
(45) Date of Patent: *Apr. 14, 2015

(54) CANNULA INSERTION DEVICE AND RELATED METHODS

(75) Inventors: Peter Gravesen, Nordborg (DK); Heiko Arndt, Flensborg (DE)

(73) Assignee: Cequr SA, Horw (CH)

( * ) Notice: Subject to any disclaimer, the term of this patent is extended or adjusted under 35 U.S.C. 154(b) by 16 days.

This patent is subject to a terminal disclaimer.

(21) Appl. No.: 12/913,311

(22) Filed: Oct. 27, 2010

(65) Prior Publication Data

US 2011/0040252 A1 Feb. 17, 2011

Related U.S. Application Data

(63) Continuation of application No. 12/250,760, filed on Oct. 14, 2008, now Pat. No. 7,846,132.

(30) Foreign Application Priority Data

Oct. 16, 2007 (DE) .......................... 10 2007 049 446

(51) Int. Cl.
*A61M 5/32* (2006.01)
*A61M 25/06* (2006.01)
*A61M 5/142* (2006.01)
(Continued)

(52) U.S. Cl.
CPC ........ *A61M 25/0606* (2013.01); *A61M 5/14248* (2013.01); *A61M 5/158* (2013.01); *A61M 25/02* (2013.01); *A61M 2005/14252* (2013.01); *A61M 2005/1583* (2013.01); *A61M 2005/1585* (2013.01)

(58) Field of Classification Search
USPC ......... 604/110, 123, 131, 132, 135, 136, 142, 604/151, 157, 158, 161, 162, 164.01, 604/164.08, 174, 198, 263, 264, 273, 506, 604/890.1, 93.01
See application file for complete search history.

(56) References Cited

U.S. PATENT DOCUMENTS

| 3,289,675 A | 12/1966 | Dunmire et al. |
| 3,714,945 A | 2/1973 | Stanley |
| 4,055,175 A | 10/1977 | Clemens et al. |

(Continued)

FOREIGN PATENT DOCUMENTS

| CA | 2159052 A1 | 4/1996 |
| EP | 0 239 721 | 10/1987 |

(Continued)

OTHER PUBLICATIONS

International Search Report and Written Opinion mailed Jul. 20, 2011, for PCT Application PCT/US2010/044996, 18 pages.

(Continued)

*Primary Examiner* — Scott Medway
(74) *Attorney, Agent, or Firm* — Goodwin Procter LLP

(57) ABSTRACT

A cannula insertion device includes a housing defining an opening for receiving therethrough a cannula and further defining a channel, and a cannula forming a lumen, the cannula adapted for sliding movement within the housing from a retracted position to an extended position. When the cannula is in the retracted position, the lumen is located remotely from the channel and the channel is in fluidic communication with the opening. When the cannula is in the extended position, the lumen is in fluidic communication with the channel.

16 Claims, 15 Drawing Sheets

(51) Int. Cl.
*A61M 5/158* (2006.01)
*A61M 25/02* (2006.01)

(56) References Cited

U.S. PATENT DOCUMENTS

| | | |
|---|---|---|
| 4,077,405 A | 3/1978 | Haerten et al. |
| 4,086,036 A | 4/1978 | Hagen et al. |
| 4,209,014 A | 6/1980 | Sefton et al. |
| 4,237,775 A | 12/1980 | Eisele |
| 4,265,241 A | 5/1981 | Portner et al. |
| 4,435,173 A | 3/1984 | Siposs et al. |
| 4,443,218 A | 4/1984 | DeCant, Jr. et al. |
| 4,447,224 A | 5/1984 | DeCant, Jr. et al. |
| 4,486,190 A | 12/1984 | Reinicke |
| 4,525,165 A | 6/1985 | Fischell |
| 4,551,133 A | 11/1985 | Zegers de Beyl et al. |
| 4,557,726 A | 12/1985 | Reinicke |
| 4,617,014 A | 10/1986 | Cannon et al. |
| 4,645,495 A | 2/1987 | Vaillancourt |
| 4,714,462 A | 12/1987 | DiDomenico |
| 4,715,852 A | 12/1987 | Reinicke et al. |
| 4,734,092 A | 3/1988 | Millerd |
| 4,747,831 A | 5/1988 | Kulli |
| 4,752,289 A | 6/1988 | Balding et al. |
| 4,755,173 A | 7/1988 | Konopka et al. |
| 4,784,577 A | 11/1988 | Ritson et al. |
| 4,784,645 A | 11/1988 | Fischell |
| 4,836,752 A | 6/1989 | Burkett |
| 4,898,579 A | 2/1990 | Groshong et al. |
| 4,920,972 A | 5/1990 | Frank et al. |
| 4,943,279 A | 7/1990 | Samiotes et al. |
| 4,994,035 A | 2/1991 | Mokros |
| 4,994,042 A | 2/1991 | Vadher |
| 4,998,918 A | 3/1991 | Mimura et al. |
| 5,011,477 A | 4/1991 | Winchell et al. |
| 5,033,714 A | 7/1991 | Winchell et al. |
| 5,085,644 A | 2/1992 | Watson et al. |
| 5,096,385 A | 3/1992 | Georgi et al. |
| 5,106,374 A | 4/1992 | Apperson et al. |
| 5,129,884 A | 7/1992 | Dysarz |
| 5,176,653 A | 1/1993 | Metals |
| 5,176,662 A | 1/1993 | Bartholomew et al. |
| 5,190,522 A | 3/1993 | Wojcicki et al. |
| 5,211,626 A | 5/1993 | Frank et al. |
| 5,224,934 A | 7/1993 | Payne et al. |
| 5,317,269 A | 5/1994 | Mills et al. |
| 5,321,392 A | 6/1994 | Skakoon et al. |
| 5,356,389 A | 10/1994 | Willing |
| 5,360,411 A | 11/1994 | Mimura et al. |
| 5,395,320 A | 3/1995 | Padda et al. |
| 5,407,431 A | 4/1995 | Botich et al. |
| 5,480,388 A | 1/1996 | Zadini et al. |
| 5,492,533 A | 2/1996 | Kriesel |
| 5,522,799 A | 6/1996 | Furukawa |
| 5,524,907 A | 6/1996 | Walser |
| 5,545,143 A | 8/1996 | Fischell |
| 5,562,629 A | 10/1996 | Haughton et al. |
| 5,584,809 A | 12/1996 | Gaba |
| 5,625,151 A | 4/1997 | Yamaguchi |
| 5,656,032 A | 8/1997 | Kriesel et al. |
| 5,681,284 A | 10/1997 | Herskowitz |
| 5,697,907 A | 12/1997 | Gaba |
| 5,720,721 A | 2/1998 | Dumas et al. |
| 5,764,034 A | 6/1998 | Bowman et al. |
| 5,791,880 A | 8/1998 | Wilson |
| 5,839,467 A | 11/1998 | Saaski et al. |
| 5,843,014 A | 12/1998 | Lattin et al. |
| 5,851,197 A | 12/1998 | Marano et al. |
| 5,897,530 A | 4/1999 | Jackson |
| 5,968,011 A | 10/1999 | Larsen et al. |
| 5,984,894 A | 11/1999 | Poulsen et al. |
| 5,989,197 A | 11/1999 | Avaltroni et al. |
| 5,993,425 A | 11/1999 | Kriesel |
| 5,997,507 A | 12/1999 | Dysarz |
| 6,009,752 A | 1/2000 | Iwata |
| 6,056,726 A | 5/2000 | Isaacson |
| 6,077,244 A | 6/2000 | Botich et al. |
| 6,325,781 B1 | 12/2001 | Takagi et al. |
| 6,355,021 B1 | 3/2002 | Nielsen et al. |
| 6,358,225 B1 | 3/2002 | Butterfield |
| 6,379,338 B1 | 4/2002 | Garvin |
| 6,416,291 B1 | 7/2002 | Butterfield et al. |
| 6,485,461 B1 | 11/2002 | Mason et al. |
| 6,520,938 B1 | 2/2003 | Funderburk et al. |
| 6,555,986 B2 | 4/2003 | Moberg |
| 6,579,267 B2 | 6/2003 | Lynch et al. |
| 6,589,229 B1 | 7/2003 | Connelly et al. |
| 6,607,509 B2 | 8/2003 | Bobroff et al. |
| 6,620,140 B1 | 9/2003 | Metzger |
| 6,647,860 B2 | 11/2003 | Savel et al. |
| 6,656,158 B2 | 12/2003 | Mahoney et al. |
| 6,656,159 B2 | 12/2003 | Flaherty |
| 6,659,980 B2 | 12/2003 | Moberg et al. |
| 6,669,669 B2 | 12/2003 | Flaherty et al. |
| 6,692,457 B2 | 2/2004 | Flaherty |
| 6,699,218 B2 | 3/2004 | Flaherty et al. |
| 6,723,072 B2 | 4/2004 | Flaherty et al. |
| 6,740,059 B2 | 5/2004 | Flaherty |
| 6,749,587 B2 | 6/2004 | Flaherty |
| 6,768,425 B2 | 7/2004 | Flaherty et al. |
| 6,830,558 B2 | 12/2004 | Flaherty et al. |
| 6,830,562 B2 | 12/2004 | Mogensen et al. |
| 6,852,094 B2 | 2/2005 | Beck et al. |
| 6,852,104 B2 | 2/2005 | Blomquist |
| 6,871,546 B2 | 3/2005 | Scheurich et al. |
| 6,892,755 B2 | 5/2005 | Black |
| 6,901,293 B2 | 5/2005 | Rogers et al. |
| 6,905,482 B2 | 6/2005 | Hochman |
| 6,923,791 B2 | 8/2005 | Douglas |
| 6,939,324 B2 | 9/2005 | Gonnelli et al. |
| 6,949,084 B2 | 9/2005 | Marggi et al. |
| 6,960,192 B1 | 11/2005 | Flaherty et al. |
| 6,969,358 B2 | 11/2005 | Baltschun et al. |
| D515,288 S | 2/2006 | Della Valle et al. |
| 6,997,907 B2 | 2/2006 | Safabash et al. |
| 7,000,806 B2 | 2/2006 | Py et al. |
| 7,018,360 B2 | 3/2006 | Flaherty et al. |
| 7,029,455 B2 | 4/2006 | Flaherty |
| 7,052,483 B2 | 5/2006 | Wojcik |
| 7,066,031 B2 | 6/2006 | Zdeblick et al. |
| 7,083,597 B2 | 8/2006 | Lynch et al. |
| 7,109,878 B2 | 9/2006 | Mann et al. |
| 7,115,111 B2 | 10/2006 | Haindl et al. |
| 7,137,964 B2 | 11/2006 | Flaherty |
| 7,144,384 B2 | 12/2006 | Gorman et al. |
| 7,207,974 B2 | 4/2007 | Safabash et al. |
| 7,291,126 B2 | 11/2007 | Shekalim et al. |
| 7,297,138 B2 | 11/2007 | Fangrow, Jr. |
| 7,303,549 B2 | 12/2007 | Flaherty et al. |
| 7,341,572 B2 | 3/2008 | Bridle et al. |
| 7,377,907 B2 | 5/2008 | Shekalim |
| 7,407,491 B2 | 8/2008 | Fangrow, Jr. |
| 7,455,663 B2 | 11/2008 | Bikovsky |
| 7,470,237 B2 | 12/2008 | Beckman et al. |
| 7,544,185 B2 | 6/2009 | Bengtsson |
| 7,569,034 B2 | 8/2009 | Lynch et al. |
| 7,771,412 B2 | 8/2010 | Anderson et al. |
| 7,846,132 B2 | 12/2010 | Gravesen et al. |
| 7,887,505 B2 | 2/2011 | Flaherty |
| 7,918,825 B2 | 4/2011 | O'Connor et al. |
| 8,628,498 B2 * | 1/2014 | Safabash et al. .......... 604/164.12 |
| 2002/0072720 A1 | 6/2002 | Hague et al. |
| 2002/0087147 A1 | 7/2002 | Hooper et al. |
| 2002/0120231 A1 | 8/2002 | Douglas et al. |
| 2002/0151332 A1 | 10/2002 | Eddy |
| 2002/0161332 A1 | 10/2002 | Ramey |
| 2002/0173769 A1 | 11/2002 | Gray et al. |
| 2002/0183693 A1 | 12/2002 | Peterson et al. |
| 2003/0109829 A1 | 6/2003 | Mogensen et al. |
| 2003/0204274 A1 | 10/2003 | Ullestad et al. |
| 2004/0059316 A1 | 3/2004 | Smedegaard |
| 2004/0092865 A1 | 5/2004 | Flaherty et al. |
| 2004/0133166 A1 | 7/2004 | Moberg et al. |
| 2004/0143216 A1 | 7/2004 | Douglas et al. |

(56) References Cited

U.S. PATENT DOCUMENTS

| | | |
|---|---|---|
| 2004/0143218 A1 | 7/2004 | Das |
| 2004/0143241 A1 | 7/2004 | Douglas et al. |
| 2004/0158207 A1 | 8/2004 | Hunn et al. |
| 2004/0167464 A1 | 8/2004 | Ireland et al. |
| 2004/0204673 A1 | 10/2004 | Flaherty |
| 2004/0216103 A1 | 10/2004 | Burky et al. |
| 2005/0010912 A1 | 1/2005 | Adolphson et al. |
| 2005/0101932 A1 | 5/2005 | Cote et al. |
| 2005/0101933 A1 | 5/2005 | Marrs et al. |
| 2005/0124936 A1 | 6/2005 | Mogensen et al. |
| 2005/0171512 A1 | 8/2005 | Flaherty |
| 2005/0182366 A1 | 8/2005 | Vogt et al. |
| 2005/0203461 A1 | 9/2005 | Flaherty et al. |
| 2005/0238507 A1 | 10/2005 | Dilanni et al. |
| 2005/0266582 A1 | 12/2005 | Modlin et al. |
| 2005/0273076 A1 | 12/2005 | Beasley et al. |
| 2006/0015076 A1 | 1/2006 | Heinzerling et al. |
| 2006/0030836 A1 | 2/2006 | Lee et al. |
| 2006/0041229 A1 | 2/2006 | Garibotto et al. |
| 2006/0129123 A1 | 6/2006 | Wojcik |
| 2006/0161108 A1 | 7/2006 | Mogensen et al. |
| 2006/0178633 A1 | 8/2006 | Garibotto et al. |
| 2006/0184121 A1 | 8/2006 | Brockman et al. |
| 2006/0229560 A1 | 10/2006 | Marano-Ford et al. |
| 2006/0264835 A1 | 11/2006 | Nielsen et al. |
| 2006/0264898 A1 | 11/2006 | Beasley et al. |
| 2006/0282290 A1 | 12/2006 | Flaherty et al. |
| 2007/0016129 A1 | 1/2007 | Liniger et al. |
| 2007/0019772 A1 | 1/2007 | Spires et al. |
| 2007/0049870 A1 | 3/2007 | Gray et al. |
| 2007/0074722 A1 | 4/2007 | Giroux et al. |
| 2007/0083153 A1 | 4/2007 | Haar |
| 2007/0088254 A1 | 4/2007 | DeStefano |
| 2007/0106218 A1 | 5/2007 | Yodfat et al. |
| 2007/0112301 A1 | 5/2007 | Preuthun et al. |
| 2007/0118405 A1 | 5/2007 | Campbell et al. |
| 2007/0185454 A1 | 8/2007 | Fangrow |
| 2007/0191773 A1 | 8/2007 | Wojcik |
| 2007/0231204 A1 | 10/2007 | Hyde et al. |
| 2007/0250007 A1 | 10/2007 | Shekalim |
| 2007/0282269 A1 | 12/2007 | Carter et al. |
| 2007/0299397 A1 | 12/2007 | Alferness et al. |
| 2008/0033361 A1 | 2/2008 | Evans et al. |
| 2008/0051710 A1 | 2/2008 | Moberg et al. |
| 2008/0051738 A1 | 2/2008 | Griffin |
| 2008/0058718 A1 | 3/2008 | Adams et al. |
| 2008/0086086 A1 | 4/2008 | Field et al. |
| 2008/0116647 A1 | 5/2008 | Anderson et al. |
| 2008/0119792 A1 | 5/2008 | Kornerup et al. |
| 2008/0119822 A1 | 5/2008 | Knauper |
| 2008/0139907 A1 | 6/2008 | Rao et al. |
| 2008/0147044 A1 | 6/2008 | Palmer et al. |
| 2008/0147050 A1 | 6/2008 | Mann et al. |
| 2008/0154205 A1 | 6/2008 | Wojcik |
| 2008/0160492 A1 | 7/2008 | Campbell et al. |
| 2008/0172030 A1 | 7/2008 | Blomquist |
| 2008/0183060 A1 | 7/2008 | Steil et al. |
| 2008/0214919 A1 | 9/2008 | Harmon et al. |
| 2008/0215006 A1 | 9/2008 | Thorkild |
| 2008/0227210 A1 | 9/2008 | Smith |
| 2008/0234630 A1 | 9/2008 | Iddan et al. |
| 2008/0243053 A1 | 10/2008 | DeStefano et al. |
| 2008/0249505 A1 | 10/2008 | DeStefano et al. |
| 2008/0294094 A1 | 11/2008 | Mhatre et al. |
| 2008/0319416 A1* | 12/2008 | Yodfat et al. .................. 604/513 |
| 2009/0099521 A1 | 4/2009 | Gravesen et al. |
| 2009/0143732 A1 | 6/2009 | O'Connor et al. |
| 2010/0017141 A1 | 1/2010 | Campbell et al. |
| 2011/0043357 A1 | 2/2011 | Peatfield et al. |
| 2011/0046558 A1 | 2/2011 | Gravesen et al. |

FOREIGN PATENT DOCUMENTS

| | | |
|---|---|---|
| EP | 0 267 041 | 5/1988 |
| EP | 0 450 186 | 2/1995 |
| EP | 0 709 104 | 5/1996 |
| EP | 0 719 564 A1 | 7/1996 |
| EP | 1177802 | 2/2002 |
| EP | 0 652 027 | 5/2006 |
| EP | 1 652 547 | 5/2006 |
| EP | 1 792 655 | 6/2007 |
| GB | 2 031 558 | 4/1980 |
| JP | 8-206199 | 8/1996 |
| WO | WO-93/05832 | 4/1993 |
| WO | WO-93/17736 | 9/1993 |
| WO | WO-93/18305 | 9/1993 |
| WO | WO-9427669 A1 | 12/1994 |
| WO | WO-96/32981 | 10/1996 |
| WO | WO-9738322 A1 | 10/1997 |
| WO | WO-98/33549 | 8/1998 |
| WO | WO-99/01731 | 1/1999 |
| WO | WO-00/06221 | 2/2000 |
| WO | WO-02/070047 | 9/2002 |
| WO | WO-02068015 | 9/2002 |
| WO | WO-2004/032990 | 4/2004 |
| WO | WO-2004/032990 A2 | 4/2004 |
| WO | WO-2007/057038 | 5/2007 |
| WO | WO-2007/140632 | 12/2007 |
| WO | WO-2007/140632 A1 | 12/2007 |
| WO | WO-2008012817 A1 | 1/2008 |
| WO | WO-2008/017329 | 2/2008 |
| WO | WO-2008/024810 | 2/2008 |

OTHER PUBLICATIONS

International Search Report for International Application PCT/IB2008/003072, mailed from the International Search Authority on Apr. 1, 2009, 5pgs.

European Office Action for 08840754.9 dated Dec. 2, 2014 (4 pages).

* cited by examiner

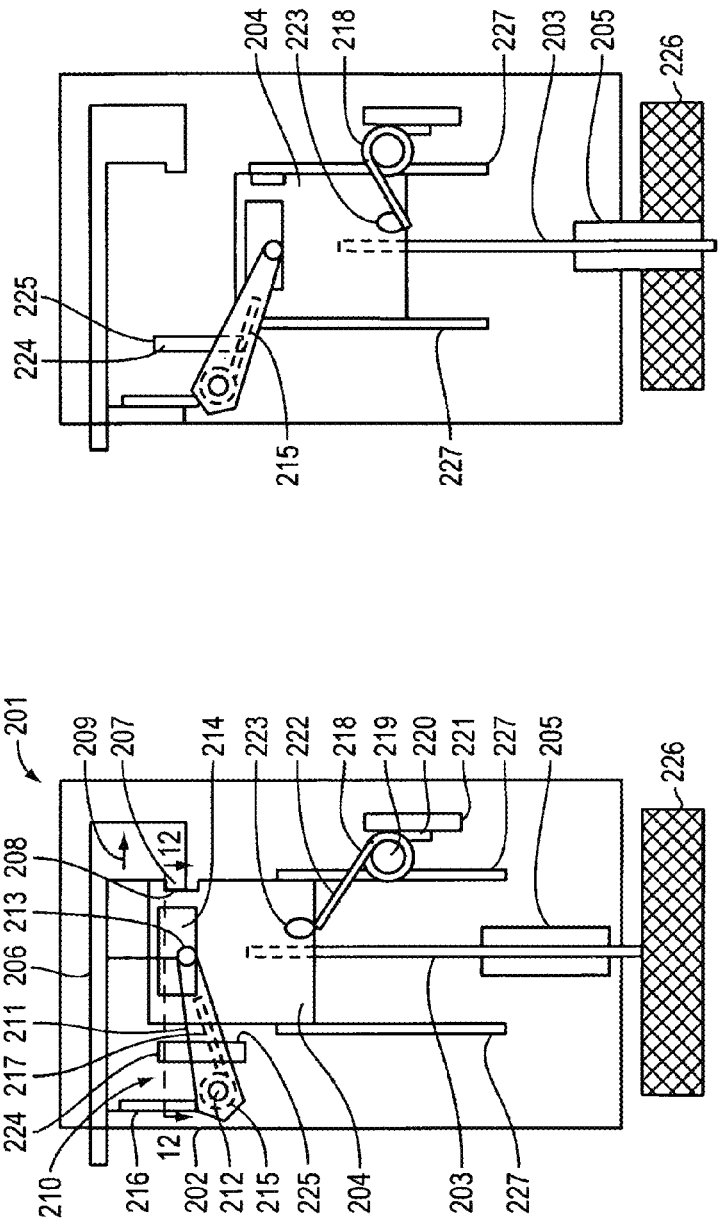

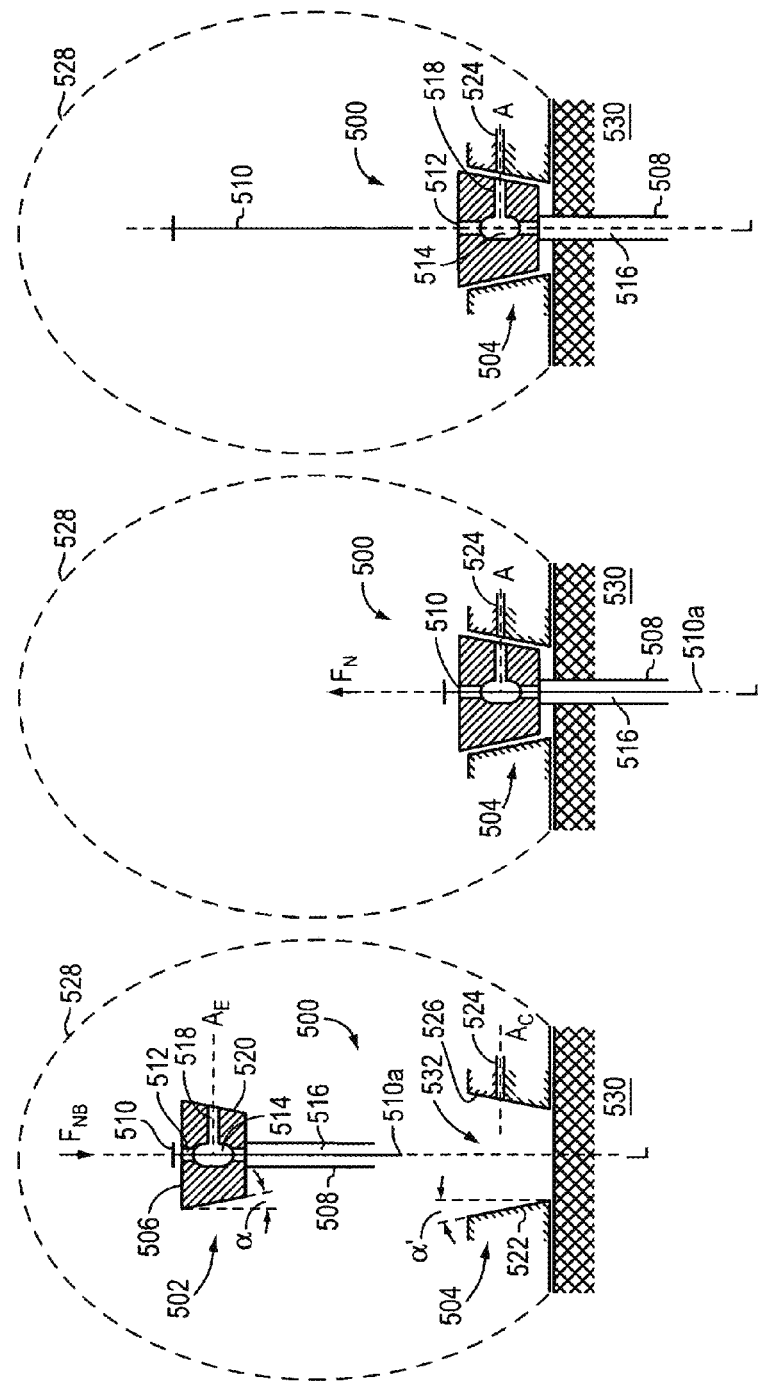

CANNULA INSERTION DEVICE AND RELATED METHODS

CROSS-REFERENCE TO RELATED APPLICATION

This is a continuation of application Ser. No.12/250,760, filed Oct. 14, 2008, the disclosure of which is hereby incorporated by reference herein in its entirety. This application claims priority to and the benefit of German Patent Application Serial No. 10 2007 049 446.9, filed Oct. 16, 2007, the disclosure of which is hereby incorporated by reference herein in its entirety.

FIELD OF THE INVENTION

This invention relates generally to systems and methods for inserting a cannula into a patient and, more specifically, to a device that automatically inserts a cannula, as well as connects the cannula lumen to a channel within an infusion device.

BACKGROUND

In many cases, it is necessary to insert a catheter or cannula into the body, or a body part of, a patient. By means of the so-inserted cannula, it is then possible to infuse medicinally-required fluid or material. Another reason for the employment of a cannula may be to aid in insertion of a micro-dialysis probe into the body.

To insert a cannula into a patient, a rigid needle is placed within the lumen of the cannula, and the needle and cannula combination is forced into the skin of a patient. Once the cannula combination is fully inserted, the needle is retracted, leaving the cannula in place. When performed manually, the penetration of the catheter-carrying needle into the body, however, may be considered uncomfortable for a patient, or may cause some other anxiety. Also, the subsequent manual withdrawal of the needle is often regarded by some patients as painful.

Automatic cannula insertion devices have been developed to address these issues. Typically, a cannula is included in a stand-alone device called an insertion or injection set. In addition to the cannula and needle, the insertion set often includes a housing to which the cannula is attached during use. The housing may have an adhesive pad for adhering the housing to the skin of the patient during use, as well as an internal void or chamber that is penetrated by an inlet and a septum. The needle passes through the septum, void, and into the lumen of the cannula. After insertion, the needle is withdrawn from the septum, which seals the void. Thereafter, a tube is connected to the inlet, thereby placing the lumen (via the void) in fluidic communication with an infusion device, intravenous (IV) drip bag, or other medical equipment. The above-described insertion sets may be acceptable for some patients, but the attached tube and medical device can be obtrusive, which may be undesirable in some cases. It would be desirable then, to incorporate the functionality of an insertion set into an infusion device to minimize the attendant tubing and complications involved in connecting the insertion set to the infusion device.

SUMMARY OF THE INVENTION

The invention relates to an insertion device for a cannula, wherein the cannula is carried on a needle, as well as a cannula configuration that allows for automatic alignment of an inlet on the cannula with a channel in an infusion device, without having to separately connect a tube thereto. In combination with a drive apparatus, the needle can be displaced from a retracted position into an extended position, thus forming a fluidic connection.

During an insertion procedure described herein, a cannula is used in conjunction with a needle. The needle is used to penetrate the body. Subsequently, the needle is withdrawn from the body, allowing the cannula to remain in its inserted position. Consequently, one advantage of the invention is to increase the comfort of a patient during the insertion and withdrawal of a catheter or cannula. This benefit may be achieved with a device for the insertion of a cannula of the type described herein, wherein the needle, after reaching its extended state, can be withdrawn quickly and automatically by a retraction apparatus.

One embodiment of the invention allows the needle to not only quickly penetrate the body tissue (i.e., blood vessel, organ, or other body part) of a patient, but due to aid from the retraction apparatus, the needle is quickly withdrawn from the body tissue and simultaneously, the inserted cannula remains within the body tissue. In this way, since the needle is relatively quickly withdrawn from the body tissue, a much more comfortable sensation is experienced than that associated with a slower insertion and withdrawal. Further, any sensation is transient. The retraction apparatus is activated, in any case, when the needle is already within the patient's tissue, that is to say, when the needle is in its extended position. Thereby, it is possible for the operator to insert the needle and its associated cannula to a sufficient depth to reach a desired position within the body tissue.

In one embodiment, the driving element or needle plunger is subject to the force of a spring. The spring can be pre-stressed and restrained by an arresting apparatus from which it is released to carry out its driving function. The spring acts upon a drive mechanism, which includes at least one first part (e.g., a plunger), which is in driving contact with a free end of the spring and the drive mechanism includes one separate second part (e.g., a support structure), indirectly activated by the spring. Thus, the second part is made slidingly displaceable in a first direction by means of the motion of the first part and, conversely, separates itself therefrom upon a movement of the first part in an opposite direction. Such an arrangement reduces the weight, which contributes to momentum during the retraction of the needle. Simultaneously, the needle, upon its movement from the retracted position into the extended position, stabilizes the cannula sufficiently when so projected, so that that the insertion procedure can be reliably carried out.

In certain embodiments, the needle, which is seated in the second part, is releasably held. Accordingly, the needle can disengage itself from the second part at the outset of a retracting motion and can be withdrawn without obstruction. In this way, the needle is not permanently affixed to the drive mechanism, an advantage which can be usefully employed to even move the needle more quickly, i.e., through more rapid increments of retractive motion.

At the time that the needle is disconnected from the second part, nothing more than the weight of the needle need be placed in motion, an advantage which allows undiminished acceleration. Since the movement of a needle within the body tissue can be uncomfortable, it is helpful if the displacement of the needle can be accelerated so that it can be removed from the tissue in a minimal amount of time.

In one embodiment, the activation of the needle is subjected to force by a separate retraction spring (compression type) dedicated thereto, which acts in a direction from the second part toward the first part. It is possible, then, that this retraction spring serving the needle can be employed to force the now-released needle away from the second part in a direction that withdraws it from the penetrated body tissue. The second part can include at least one holding element that retains the needle therein, and permits the needle to be subsequently retracted from an extended position. The concept of "retraction" or "withdrawal," as used herein, is used to describe removal of the needle from the lumen of the cannula after full insertion or extension of the cannula. The method of construction of the holding element, that is, as to whether its retaining characteristic is due to mechanical, magnetic, or other induced forces, is of secondary importance for the purpose of this description. During the interim within which the needle has not yet reached its extended position, the holding element acts to affix the needle within the second part. As soon as the second part has reached its final and extended position, the retention of the needle is no longer necessary. Accordingly, at this time, the holding element releases the needle, so that it departs from the second part and extricates itself therefrom.

In one embodiment, the holding element is located in the exposed surface of an end of the second part, from which the needle projects. From this end surface of the second part, when in extended position, the tip of the needle comes into contact with another surface. This so designated "other surface" can well be a surface of the patient's tissue, wherein the cannula is in the process of being inserted. Otherwise, the contacted surface can even be a lining of a device housing. In any case, by means of an impact of the second part against a target surface, the holding element is released, i.e., the retention of the needle therein is ended.

In one embodiment, the first part possesses an activation element, which, at the completion of needle extension, acts upon the needle holding element. In this case, the first part is employed to relieve the holding element of the second part from its retaining function. By means of the mechanical structure of the holding element the needle is released when the position of the holding element changes. If the principle of construction of the holding element is electromagnetic in character, then the activation means may open a switch, which will interrupt a supply of current to the magnetic system. In such a case, the magnet becomes deprived of its power. Additionally, it is contemplated to displace a working magnet thereby terminating its holding ability. Additional methods for this removal of holding power are contemplated.

In an embodiment of the invention, the activation means of the first part and also the holding element possess complementary, coacting, inclined surfaces. Motion of the activation means toward the holding element, which is carried out in a direction parallel to the needle, can be diverted to a motion not parallel, but rather angular therefrom. In this alteration, the angular direction could even be at a right angle.

The needle is supported by the said retraction spring to lie against the first part. This constructive support can be used with or without a holding element. The retraction spring assures that the needle can be secured by means of one or more projections on the second part. This securement would hold the needle in place during the movement of the drive mechanism. When the needle and catheter begin to penetrate into the body tissue, the needle itself is subjected to a reaction force, which, without an element for holding, finally causes the needle to act contrary to the force of the retraction spring. Nevertheless, by means of an appropriate dimensioning of the retraction spring, arrangement can be made such that the needle-catheter combination penetrates sufficiently far into the subject body tissue.

The first part may possess a second holding means to which the needle becomes secured during a withdrawal from the extended position. This holding means retains the needle firmly within the first part, so that the needle retracts by means of the reversing motion of the first part of the drive mechanism.

In this arrangement, a second holding means consists of a cavity in the first part. The needle, or if necessary, a thickened section of the needle, is then simply retainingly inserted into the first part and subsequently held there by a force of friction. The necessary frictional forces can be increased by an appropriate surfacing of the interior of the cavity and/or increasing the size of the active exterior of the needle.

The first part and the second part are located in a housing. This housing possesses in the area remote from the drive spring, an end face that blocks the travel of the second part. If the second part makes contact with the end face of the housing, or places itself very close thereto, it will be held in position by the above described holding means. This prevents the second part from following the first part as it withdraws.

A storage means for medicaments or a communicating fluidic connection for the cannula is located in the second part. In one embodiment, the second part is secured to the cannula, so that after the withdrawal of the needle, the cannula remains in its extended position in the tissue of the patient. The medicament can then be infused through the cannula into the body. An input or outtake branching can also be joined to the cannula line. By means of the input or outtake device, a medicament can be applied or blood or the like can be withdrawn from the body.

The drive mechanism functions with the aid of an inclined surface on which is formed a path for movement of the needle, since the inclined surface moves in a direction transverse (or angular) to that of the needle. This path, which accommodates the perpendicular travel of the needle, ends in a steplike termination. With such a termination as described, the functional movement of the needle is thus decoupled from its penetrative direction. The needle is forced by the inclined surface and accordingly slides along this inclined surface, being augmented by the intervention of the drive mechanism. Because of the inclined surface, the needle is subjected to an angular resultant force, which causes the needle to move. Upon an activation of the drive mechanism, an additional force may be applied to alter the direction of motion of the needle.

The above "step" is formed by a recess in the inclined surface. The needle, or an integral element thereof, drops into the recess once it has reached its final, extended position. This recess also blocks any additional movement of the inclined surface. The inclined surface possesses a helical configuration and moves in a rotatable body. This rotatable body comprises, for example, a cylindrical shape, and can form a part of the drive mechanism. When this body is rotated, then an effective area of the inclined surface forms a slidingly spiral path for the needle alone or for both the needle and the drive mechanism together. As the needle moves from its withdrawn position into its extended position it may move with the drive mechanism. In this way, a relatively long length of the sliding path on the helical inclined surface is achieved with minimum space and an excessive dimensioning of the insertion mechanism is thereby avoided.

In one aspect, the invention relates to a cannula insertion device including a housing defining an opening for receiving therethrough a cannula and further defining a channel, and a cannula forming a lumen, the cannula adapted for sliding movement within the housing from a retracted position to an extended position, wherein when the cannula is in the retracted position, the lumen is located remotely from the channel and the channel is in fluidic communication with the opening, and when the cannula is in the extended position, the lumen is in fluidic communication with the channel. In an embodiment of the above aspect, the cannula insertion device further includes a base connected to the cannula, the base defining an internal chamber in fluidic communication with the lumen. In another embodiment, the base further defines a chamber extension in fluidic communication with the internal chamber. In yet another embodiment, when the cannula is in the extended position, the chamber extension is aligned with the channel. In still another embodiment, a wall of the base defines the chamber extension.

In another embodiment of the above aspect, the base includes a resilient sheath, the sheath defining a port substantially aligned with the chamber extension. In another embodiment, when the cannula is in the extended position, the port is aligned with the channel. In yet another embodiment, when the cannula is in the extended position, the sheath seals the opening. In still another embodiment, the cannula insertion device further includes a plunger for driving the cannula from the retracted position to the extended position. In another embodiment, the cannula insertion device further includes a needle disposed in the lumen when the cannula is in the retracted position. In another embodiment, the needle is adapted to be automatically withdrawn from the lumen when the cannula is in the extended position. In another embodiment, the needle is adapted to be automatically disconnected from the plunger when the cannula is in the extended position.

In another aspect, the invention relates to a method of inserting a cannula, the method including the steps of providing a housing defining an opening for receiving therethrough a cannula and further defining a channel, providing a cannula forming a lumen, the cannula adapted for sliding movement within the housing from a retracted position to an extended position, and extending the cannula from the retracted position, in which the lumen is located remotely from the channel and the channel is in fluidic communication with the opening, to the extended position, in which the lumen is in fluidic communication with the channel. In an embodiment of the above aspect, the method further includes the step of piercing a skin of a patient with a needle and the cannula as the cannula moves from the retracted position to the extended position. In another embodiment, the method further includes the step of withdrawing the needle from the lumen automatically when the cannula is in the extended position. In yet another embodiment, a plunger extends the cannula from the retracted position to the extended position, the plunger in contact with the needle. In still another embodiment, the method includes the step of disconnecting the needle from the plunger when the cannula is in the extended position. In another embodiment, the method includes the step of sealing the opening with the cannula when the cannula is in the extended position.

BRIEF DESCRIPTION OF THE FIGURES

Other features and advantages of the present invention, as well as the invention itself, can be more fully understood from the following description of the various embodiments, when read together with the accompanying drawings, in which:

FIG. 9 is a schematic side view of an insertion device in a retracted position in accordance with another embodiment of the invention;

FIG. 10 is a schematic side view of the insertion device of FIG. 9 in an extended position;

FIGS. 20A-20C are schematic side sectional views depicting a method of inserting an automatically-aligning cannula in accordance with one embodiment of the invention.

DETAILED DESCRIPTION

Figure 1:
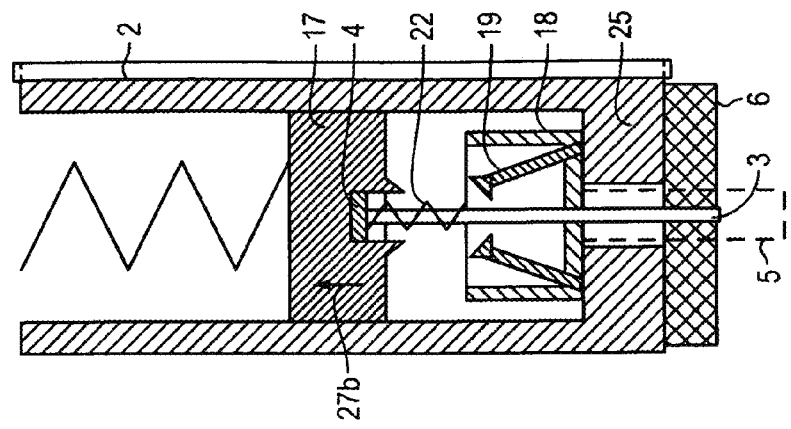
FIG. 1 is a schematic sectional side view of an insertion device in a retracted position in accordance with one embodiment of the invention.

FIG. 1 depicts an embodiment of an insertion device for a catheter 1 having a housing 2, within which a needle 3 is affixed by a needle holder 4. On the end remote from the needle holder 4, the needle 3 carries a catheter or cannula 5. In this document, the terms "catheter" and "cannula" are used interchangeably and without limitation to described any tube-like implement to deliver fluids to any body part of a patient. In the attached figures, for the sake of clarity, the representation of the catheter 5 is enlarged. In general, the diameter of the catheter 5 is only slightly larger than the outside diameter of the needle 3.

The needle 3, in a manner not shown, is so enveloped by a guide in the housing 2, that it can only move in a direction parallel to its longitudinal axis L. The design allows the needle 3 to be displaced into an extended position. In this extended position of the needle 3, depicted in FIG. 2, the catheter 5 is positioned at least partially outside the housing 2 and thus penetrating into body tissue 6. Designated here as "body tissue" is to be understood, for example, the skin, vein, or organ of a patient.

In order to move the needle 3 in conjunction with the catheter 5, a drive mechanism V is provided. Alternative drive mechanisms are also described in FIGS. 6-13. The drive mechanism V depicted in FIGS. 1-3 possesses a drive spring 16 which powers the drive mechanism V. Described in greater detail, the drive spring 16 acts upon a first part or plunger 17, which is positioned against a second part or support structure 18. This support structure 18 can be loosely affixed to the first part or plunger 17 or, alternately, secured thereto by an additional spring (not shown), which would abut the housing 2. In another embodiment, a holding means can be installed to combine the first and second parts, respectively 17 and 18. This holding means may be any type of chemical, mechanical, electromagnetic, or other fastener.

In any case, the two parts 17 and 18 are made to move under the force of the drive spring 16 in the direction of the tissue 6 of a patient, as depicted by arrow 27*a*.

Figure 2:
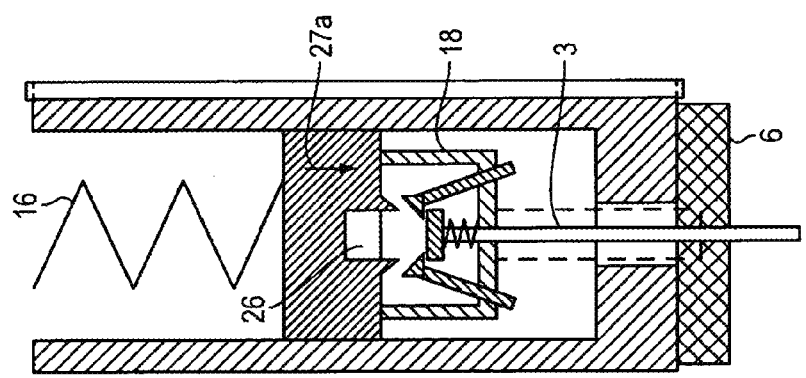
FIG. 2 is a schematic sectional side view of the insertion device of FIG. 1 in an intermediate position.

In the support structure 18, the needle 3 is retained, in particular by means of two needle holding elements 19. These holding elements 19 project outward from the patient proximal end face 20 of the support structure 18. The two holding elements 19 each include endwise, remote from the end face 20, a hook 21, which is shown in FIGS. 1 and 2 as located on the top of the needle holder 4. The needle holder 4 supports itself against the support structure 18 by means of a retraction spring 22. However, this needle holder 4 can only be displaced in the direction of the plunger 17 to such extent that it is permitted by the needle holding elements 19.

Each of the hooks 21 on the needle holders 19 possesses on the end proximate to the plunger 17 an inclined outer surface 23. The plunger 17 is equipped on the side proximate to the support structure 18 with projections having inclined surfaces 24, which are complementary to the above-mentioned surfaces 23. When the parts 17 and 18 are sufficiently displaced by the force of the drive spring 16, the needle holding elements 19, projecting out of the end face 20 of the support structure 18, make contact with a base wall 25 of the housing 2. The holding elements 19 are detachably connected to the support structure 18. Accordingly, as the holding elements 19 make contact with the base wall 25, spring 16 continues to drive support structure 18 toward the base wall 25, causing the holding elements 19 to detach from the support structure 18. The continued movement of the support structure 18 in the direction of the base wall 25 forces the needle holding elements 19 in the direction of the plunger 17, until the complementary inclined surfaces 23, 24 contact one another. At this point, the holding elements 19 are displaced outward and thus free the needle holder 4 from the support structure 18. With this arrangement, the needle 3, activated by the force of a retraction spring 22, is moved in the direction of the plunger 17. At this point of operation, the compressed retraction spring 22 initially displaces the needle 3 with a relatively greater acceleration. Accordingly, the needle 3 is forced backward out of the body tissue 6.

The first part includes a recess 26, into which the needle holder 4 can retreat under the force of the retraction spring 22. This recess 26 is, in this case, simply shown as a cavity sized to match the needle holder 4. Other types of recesses are also contemplated. In function, the recess 26 accepts the needle holder 4 with the thereto affixed needle 3 and, at the same time, firmly secures the needle 3, so that, after the initial movement, the needle 3 can be retracted along with plunger 17 out of its extended position. The needle holder 4 may be secured within the recess 26 by mechanical, chemical, magnetic, friction, or other means. At the same time, the needle 3 is relieved of the catheter 5, which remains in its embedded position in the patient's tissue 6. This displacement of parts is shown by the arrow 27*b*.

Figure 3:
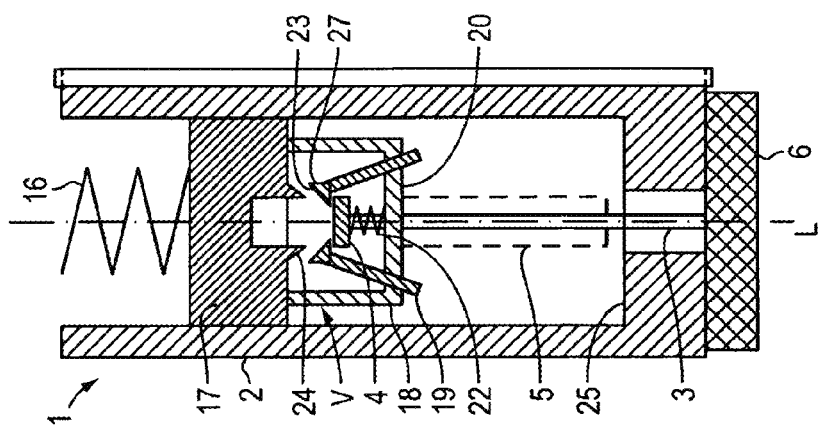
FIG. 3 is a schematic sectional side view of the insertion device of FIG. 1 in a second intermediate position.
Figure 4:
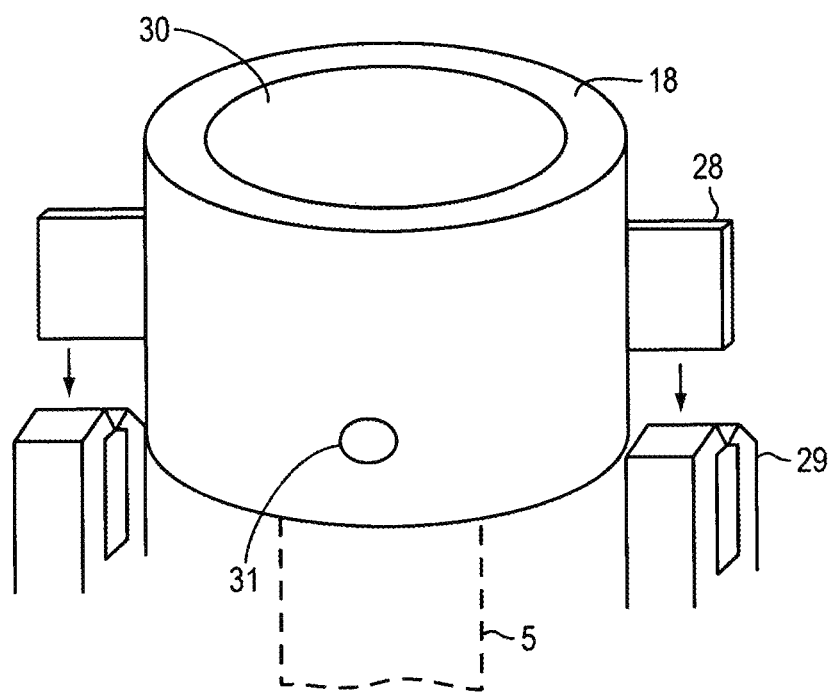
FIG. 4 is a schematic perspective view of a portion of an insertion device in accordance with another embodiment of the invention.

The support structure 18, in this state of the operation, remains in the position shown in FIG. 3. The support structure 18 may be equipped with lateral lugs 28, which may fit into clamps 29, when the support structure 18 is fully extend and the catheter inserted into the patient tissue 6. These lugs 28 and clamps 29 are depicted in FIG. 4. The clamps 29 firmly secure to the lugs 28, so that the support structure 18 lies fixedly on the base wall 25 of the housing 2. In an alternative to the depicted lugs and clamps, matching male and female ports may be located on the support structure 18 and base wall 25 to hold the support structure 18 in place against the base wall 25. Additionally, lugs be used in embodiments of the catheter insertion device that do not utilize a support structure. For example, the automatically aligning cannula depicted in FIG. 14 utilizes lugs for alignment, secured directly to the catheter base. This embodiment is described in more detail below.

Additionally, means can be provided that exert a clamping force between the support structure 18 and the needle 3 or between the catheter 5 and the needle 3. In such a case, during a displacement of the support structure 18, forces would be transferred to the needle 3, which would be sufficient to firmly align the needle 3 in place during its penetration into the body tissue 6. When the catheter 5 and the needle 3 attain their desired penetration, i.e., reach the extended position, then the clamping of the holding means is relaxed and the retaining friction attributable thereto against the needle 3 is removed, so that the needle 3 is free to be withdrawn in the manner described above.

The support structure 18 may possess a stand-alone storage means for medicaments, whereby the medicaments can be delivered through the catheter 5. Alternatively, the cannula insertion device described herein may be integrated with a medication delivery device having its own storage means of medicament. In such an embodiment, the support structure 18 can be provided with an opening 31, by means of which an input of medicament supply or the like can be effected. Such an opening would also permit the input or removal of materials, for instance of blood or sera. Such an embodiment is described in more detail with regard to FIGS. 14-20C.

Figure 5:
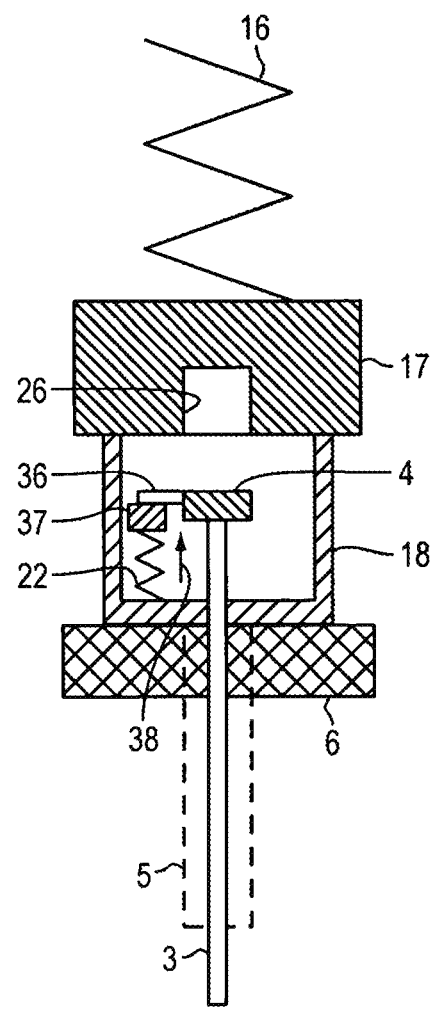
FIG. 5 is a schematic sectional side view of an insertion device in accordance with another embodiment of the invention.

FIG. 5 shows an alternative embodiment of the needle retraction system depicted in FIGS. 1-3. In this embodiment, needle holder 4 is provided with a lateral projection 36, which is acted upon by the refraction spring 22. A release apparatus 37 prevents the refraction spring 22 from retracting the needle 3 prior the needle 3 reaching the extended position depicted in FIG. 5. Once the needle 3 is in the extended position, however, the release apparatus 37 frees the retraction spring 22 and the needle 3 is withdrawn from the body tissue 6 in the direction of arrow 38. In the withdrawn position, the needle holder 4 would be secured within the recess 26. As the plunger 17 retracts, the needle 3, retained in the recess 26, is thereby fully withdrawn from the tissue 6.

Figure 7:
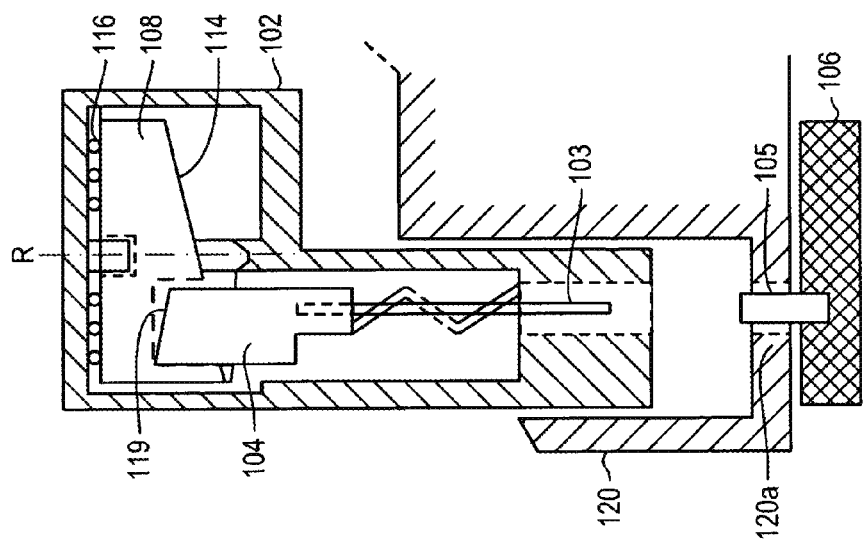
FIG. 7 is a schematic side view of the insertion device of FIG. 6 in a withdrawn position.
Figure 6:
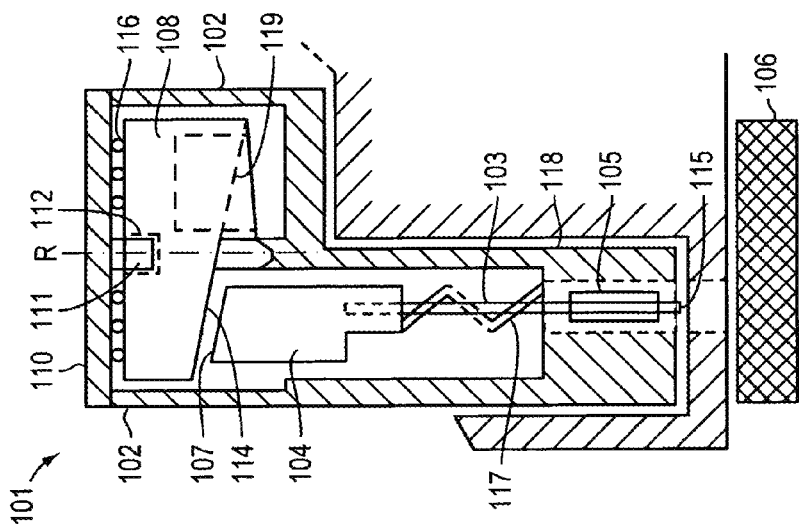
FIG. 6 is a schematic side view of an insertion device in a retracted position in accordance with another embodiment of the invention.
Figure 8:
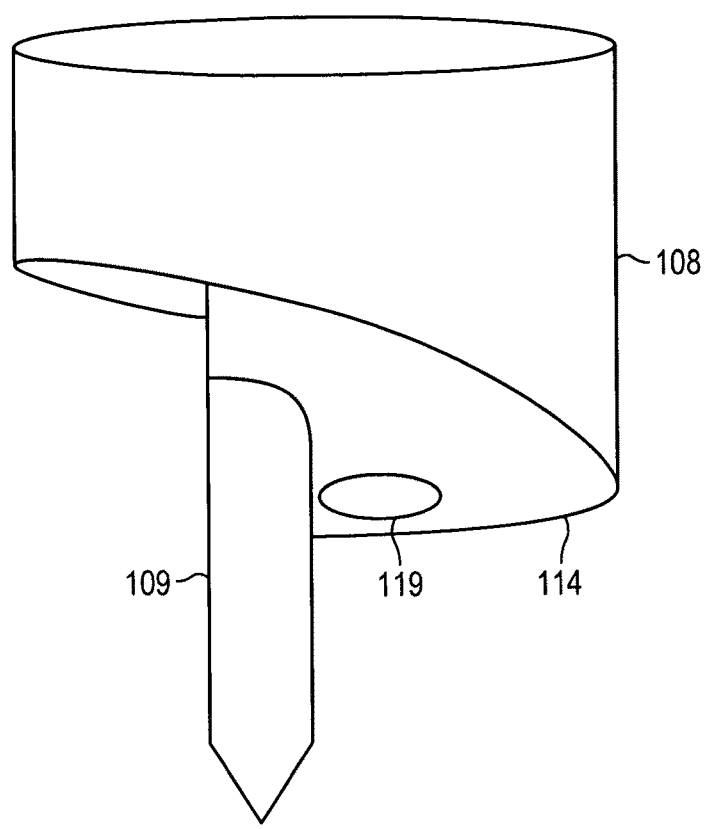
FIG. 8 is a schematic perspective view of an insertion ramp in accordance with one embodiment of the invention.

The insertion device 101 for a cannula, shown in FIGS. 6-8, includes a housing 102, in which the needle 103 coacts with needle holder 104 and cannula 105. Conveniently, a combination of the needle 103 and the needle holder 104, for example, could be constructed as a lancet. In this embodiment, the needle holder 104 is shown as a one-piece object. This could otherwise be made as a combination with the two parts 17 and 18, in the manner presented and explained in FIGS. 1-3. The needle holder 104 includes a contacting surface 107 on the end remote from the needle 103.

A cylindrical insertion ramp body 108 is located within the housing 102. The ramp body 108 is provided with a pin 109, about which it can rotate within the housing 102. Additionally, a cover 110 for the housing 102 has a positioning pin 111 which is designed to penetrate into a recess 112 in the ramp body 108, so that the ramp body 108 can align itself on both axial ends (pin 111 and pin 109 form an axis R around which the ramp body rotates) to prevent dislocation or skewing of the body 108. The housing cover 110 is preferably adhesively affixed to the housing 102 or it may be welded thereto; other methods of connection are contemplated.

The ramp body 108 includes an inclined, helically disposed surface 114 which is provided with a path for movement of an object thereon. For the sake of clarity, a separation is depicted between the needle holder 104 and the ramp body 108. In reality, the needle holder 104 lies directly on, and in complementary contact with, the helical surface 114 of the ramp body 108.

As the ramp body 108 rotates about its axis R, the needle holder 104 slides along the surface 114, forcing the needle 103 and cannula 105 downward (as depicted in FIGS. 6-7) such that the penetrative needle tip 115 exits the housing 102. As the tip 115 penetrates the tissue 106, the catheter 105 is inserted into the tissue 106.

The degree of force in the drive mechanism for the rotation of the ramp body 108 is furnished by a drive spring 116, which is designed to produce a torsion force about the axis R. Consequently, this drive spring 116 is provided with an end (not shown) abutting the housing 102 and having the other end affixed to the ramp body 108. A releasable arresting element (not shown) retains the ramp body 108 against the force of the prestressed drive spring 116. After the release of the arresting holding element, the ramp body 108 rotates in reference to the needle holder 104 by the force of the drive spring 116. This rotation displaces the needle holder 104 and therewith the needle 103 in the direction of body tissue 106.

The needle holder 104 is supported by means of a retraction spring 117, which abuts against the housing 102 at a section 118 thereof. This housing section 118 is proximate the cannula 105, when the needle 103 is placed in the retracted position as shown in FIG. 6. The retraction spring 117 also assures that the needle holder 104 is in contact with the inclined, helical surface 114 and that such contact is maintained. Upon rotation of the cylindrical body 108, the retraction spring 117 is additionally stressed. This spring is designed in an open spiral manner, which may surround the needle 103 lying between the section 118 of the housing and the needle holder 104. This refraction spring 117 can also act upon another location on the needle holder 104, especially on the first part 17 as seen in the FIGS. 1-3.

During the rotation of the ramp body 108, the contacting surface 107 of the needle holder 104 lies on a predetermined, circularly running path on the inclined surface 114. At the end of this circular running path, the ramp body 108 drops off as a recess 119, which is so dimensioned that the needle holder 104 can fit therein, as depicted in FIG. 7. Accordingly, it is only possible for the ramp body 108 to rotate until the needle holder 104 secures itself within the recess 119.

The needle 103, with the cannula 105, is now inserted into the body tissue 106 by the force of the driving spring 116. The lift of the needle holder 104, which is created by the inclined surface 114, is sufficient to serve for this purpose. As soon as the ramp body 108 has sufficiently rotated so as to align the recess 119 with the needle holder 114, no further movement of the needle 103 into an extended position may occur. Instead, a retraction motion now occurs, powered by the force of the retraction spring 117. Since the needle holder 104 drops off the inclined surface 114 into the recess 119, the retraction movement is instantaneous. Simultaneously, the ramp body 108 ceases its rotation, due to the fact that the needle holder 104 is now seated in the said recess 119, as depicted in FIG. 7.

As soon as the needle 103 has set the cannula 105 within the body tissue 106 and has been withdrawn, the housing 102 can be lifted away from the body tissue 106. In the presently described embodiment, an infusion apparatus 120 containing the housing 102 is depicted. When the housing 102, as mentioned above, is lifted away from the infusion apparatus base 120a, then the cannula 105 is freely accessible. The cannula 105 may then be connected to an infusion channel (not shown). FIG. 8 shows the ramp body 108 with the recess 119 in the inclined surface 114 as well as the positioning pin 109.

Another embodiment of a device for insertion and retraction of the needle is shown in the FIGS. 9-13. The insertion device 201 includes a housing 202, in which a needle 203 is located along with a needle holder 204 and a catheter 205. The needle holder 204 is secured in its position in the housing 202 by a holding means 206. The holding means 206 has a projection 207 which, when inserted into a recess 208 on the needle holder 204, prevents activation of the device 201. The holding means 206 is movable in the direction shown by arrow 209, which allows the needle holder 204 to be released. The needle holder 204 can, in turn, incorporate both parts 17 and 18, as depicted in FIGS. 1-3. The holding apparatus 206 can then successfully act upon the plunger 18.

A drive mechanism 210 has a lever 211, which can pivot about a pin 212. The lever 211 has further a rod 213, which enters into a cavity 214 in the needle holder 204. As depicted, the lever 211 is subjected to clockwise rotation (compare FIGS. 9 and 10) by the force of a driving spring 215. This driving spring 215 has one termination as a first leg 216 that abuts the housing 202 and also includes a second leg 217 that acts upon the lever 211. A retraction spring 218 is placed about an axial pin 219. This retraction spring 218 has a first leg 220 that abuts a housing secured projection 221 and also includes a second leg 222 that acts upon a pin 223 that projects from the needle holder 204. The retraction spring 218 exerts a lesser force upon the needle holder 204 than does the driving spring 215.

The position of the driving spring 215 is controlled by a guide member 224, which is formed by the surface of a housing projection 225. The projection 225 has a limited longitudinal dimension which runs parallel to the needle 203. To insert the cannula 205 into body tissue 226, the infusion device 120 first is placed against the body tissue 226. The holding means 206 is moved in the direction of the arrow 209, so that the projection 207 is brought out of contact with the recess 208 in the needle holder 204.

Thereafter, the needle holder 204 is displaced in a direction toward the body tissue 226 by means of the force of the driving spring 215. Guides 227 may direct the movement of the needle 203 in a straight line toward the body tissue 226. As the driving spring 215 forces the needle holder 204 into the extended position, the driving spring 215 slides along the projection 225. In accord with the FIGS. 9-11, the driving spring 215, lies between the projection 225 and the needle holder 204, as seen perpendicular to the plane of the drawing, thus being behind the needle holder 204, as depicted in FIGS. 12 and 13.

FIG. 10 depicts the needle 203, with its attached cannula 205, in an extended position, so that the cannula 205 is shown as inserted into the body tissue 226. The force necessary for this action is derived from the driving spring 215 which has been prestressed. During its movement from the retracted position (FIG. 9) to the extended position (FIG. 10) the movement of the driving spring 215 is regulated by the guide 224.

When the needle reaches the extended position, the driving spring 215 drops away from the guide 224 and the projection 225, so that it then exerts no force against the needle holder 204. This is shown in FIGS. 12 and 13.

Figure 12:
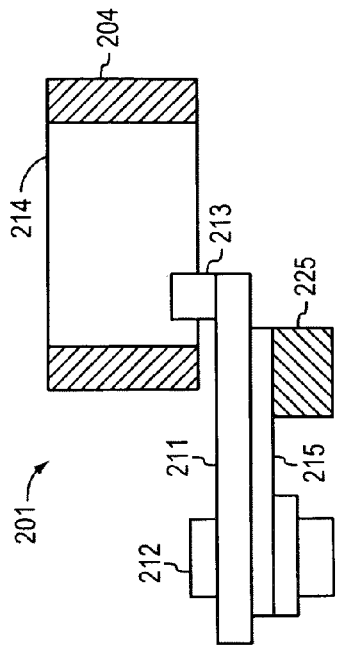
FIG. 12 is a schematic top sectional view of the insertion device of FIG. 9.
Figure 13:
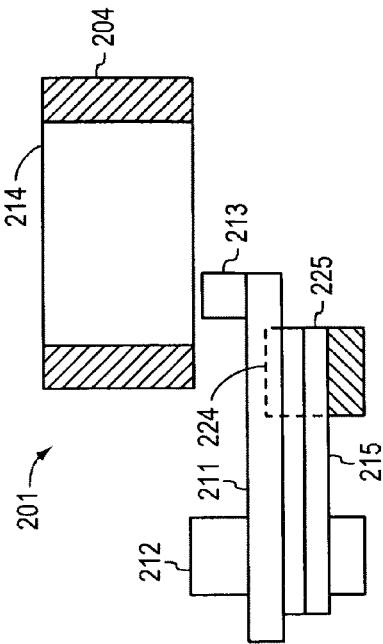
FIG. 13 is a schematic top sectional view of the insertion device of FIG. 11.

FIG. 12 depicts a top view of the insertion device 201 in the retracted position. The rod 213 is located within the recess 214 of the needle holder 204, and therefore, in contact with the needle holder 204. Accordingly, the driving spring 215 is held actively against the guide 224 of the projection 225.

Figure 11:
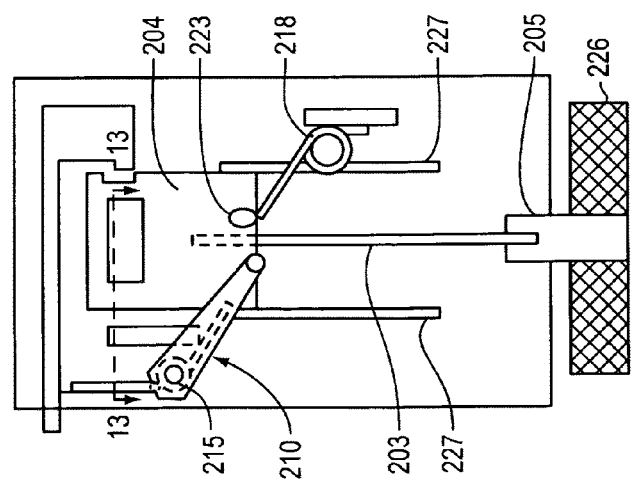
FIG. 11 is a schematic side view of the insertion device of FIG. 9 in a withdrawn position.

FIG. 13 depicts the insertion device 201 in the withdrawn position. Here, the rod 213 has lost engagement with the recess 214, due to the termination of the projection 225, and corresponding loss of engagement between the guide 224 and the driving spring 215. The operative connective relationship between the needle holder 204 and the drive unit 210 (FIG. 11) has been interrupted. This occurs at the time the needle 203 is in the extended position. Once the operational relationship between the driving unit 210 and the needle holder 204 has been interrupted, the retraction spring 218 is able to act upon the needle holder 204. As shown in FIG. 11, this causes the needle 203 to be returned to the withdrawn position. The refraction spring 218 has the ability to receive a small, pre-stressing force. However, its prestressing is generally due to the movement of the needle holder 204. The force of the retraction spring 218 may be effectively smaller than that of the driving spring 215.

In another embodiment, it is possible to permit a spring (not shown) to act transversely to the direction of driving movement of the insertion device 201, delivering force to lever 211 and/or to the driving spring 215. In this case, when the projection 225 terminates, the lever 211 and/or the driving spring 215 can be moved transverse to the direction of movement of the needle 203. It is further possible that an additional guide may be provided, which would be placed on that end of the lever 211, which is opposite the projection 225 and which would move the lever 211 and/or the driving spring 215 out of the position of FIG. 12 and into the position shown in FIG. 13.

Figure 14:
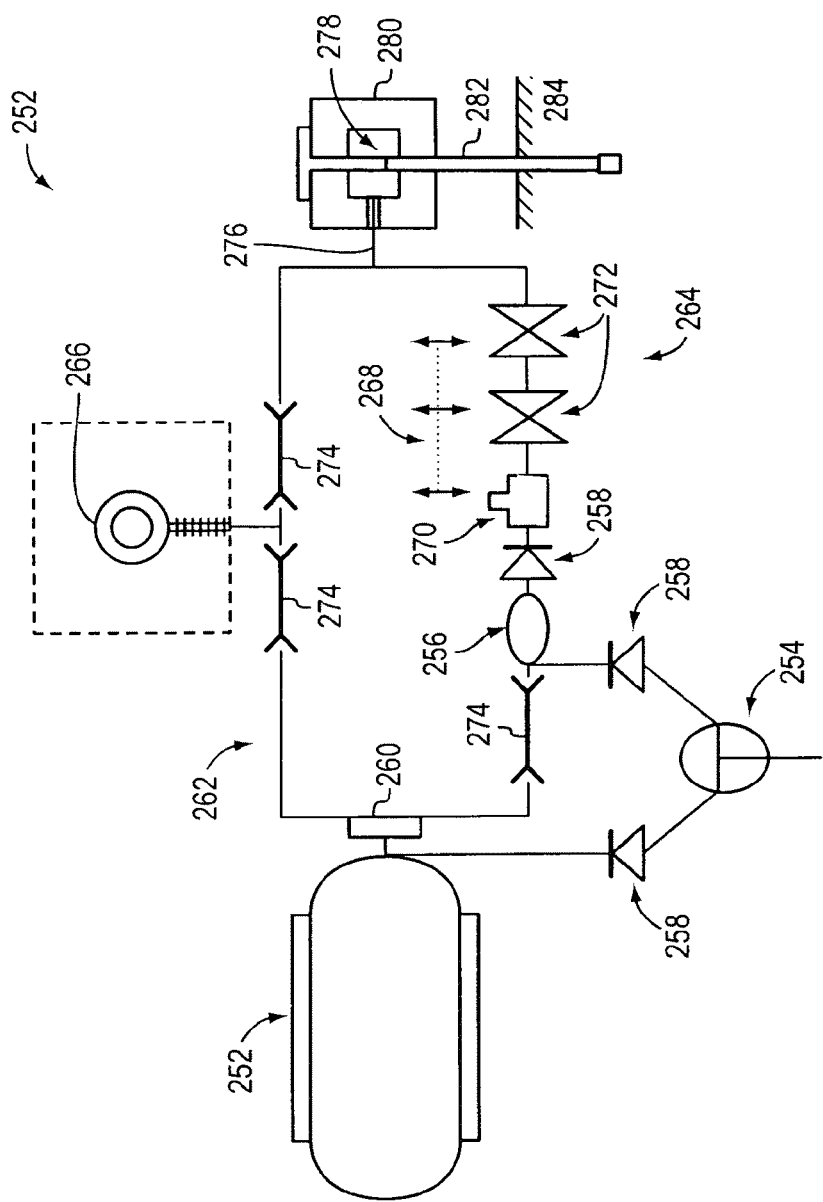
FIG. 14 is a schematic diagram of an exemplary infusion device microcircuit.

FIG. 14 is a schematic diagram of an exemplary infusion device microcircuit 250. The various cannula insertion devices described above may be utilized with the depicted microcircuit, or similar microcircuits, to establish a fluidic connection between the microcircuit 250 and a patient. Other infusion devices having microcircuits are described in U.S. Published Patent Application No. 2005/0165384, published Jul. 28, 2005, the disclose of which is hereby incorporated by reference herein in its entirety. The microcircuit 250 includes a reservoir 252 that is, in this case, comprised of an elastomer bladder. A fill port 254 is used to introduce insulin to the microcircuit 250. In this microcircuit 250, introducing insulin via the fill port 254 fills both the reservoir 252 and a variable-volume bolus reservoir 256. Check valves 258 prevent back-flow of insulin in a number of locations.

During use, insulin is forced from the reservoir 252 by the elastomer bladder, through a filter 260, and into two parallel flowpaths, a basal flowpath 262, and a bolus flowpath 264. The basal flowpath 262 delivers a constant dose of insulin to a user; the bolus flowpath 264 delivers a bolus dose of insulin to the user as needed or desired by the user. The basal flowpath 262 includes a pressure sensor 266 or other flow sensor in communication with the flowpath 262. To deliver a bolus via the bolus flowpath 264, the user presses a button 268 that drives a single stroke (delivering a single dose) of a bolus displacement chamber 270 and opens two valves 272. The valves 272 are in series for safety purposes. Flow restrictors 274 dictate the fluid flow through the flowpaths 262, 264. The parallel flowpaths 262, 264 join at a common channel 276 just before an internal chamber or a cannula void 278. The cannula void 278 is formed in a cannula base 280, which allows a point of connection to a cannula 282. The cannula 282 extends below the skin 284 of a user, thus delivering the insulin subcutaneously. In the following figures, embodiments of cannulas are described that may be used in conjunction with the insertion devices described herein to automatically form fluidic connections within devices having microfluidic circuits.

Figure 15A:
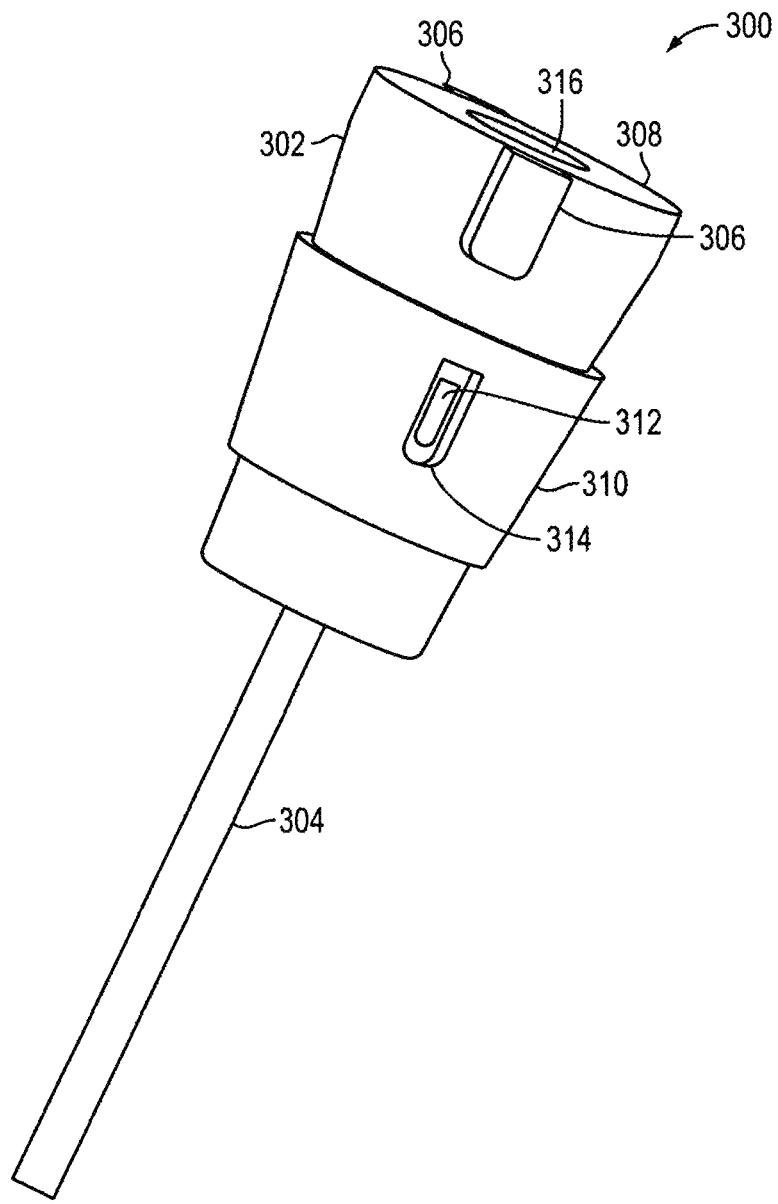
FIG. 15A is a schematic perspective view of an automatically-aligning cannula in accordance with one embodiment of the present invention.

FIG. 15A is a schematic perspective view of an automatically-aligning cannula 300, that includes two major components: a cannula base 302 and a cannula 304 secured thereto. The cannula base 302 includes one or more lugs 306 that project outward from the base 302. In the depicted embodiment, two lugs 306 are located flush with a top surface 308 of the base 302, although other locations are contemplated depending on the configurations of a housing well (described below). A resilient sheath 310 surrounds the base 302 and serves at least two purposes. First, it helps form a friction fit between the aligning cannula 300 and a housing well, when the cannula is in the extended position. Second, it helps form a seal at the interface between a chamber extension 312 (that communicates with a chamber within the base 302) and a channel located within a device housing (described below). A port 314 in the sheath 310 aligns with the chamber extension 312. The top surface 308 of the base 302 defines a void 316 for passage therethrough of the insertion needle. A self-sealing septum seals the void 316 to prevent leakage of fluid from the internal chamber once the insertion needle is removed.

Other configurations of sheaths are also contemplated. Alternative sheaths may entirely encase the catheter base, or may cover a discrete area of the base, generally surrounding the chamber extension that penetrates the wall of the base. In an alternative embodiment of the catheter base, the base itself may be entirely constructed of resilient material. In such a case, a more rigid top (e.g., in the form of a laminate construction) and lugs may be desirable to ensure that the insertion mechanism can properly exert a driving force against the base.

Figure 15B:
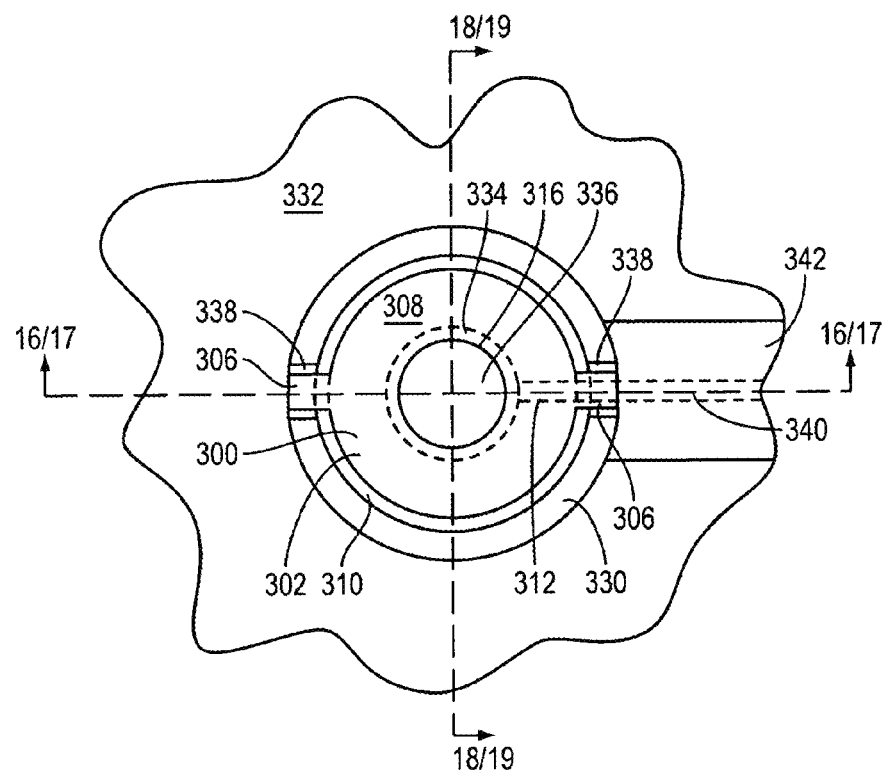
FIG. 15B is a schematic top view of the cannula of FIG. 15A.

FIG. 15B is a schematic top view of the automatically-aligning cannula assembly of FIG. 15A. In the extended position, the cannula base 302 of the automatically-aligning cannula 300 is secured within a housing well 330, due to compression of the resilient sheath 310 surrounding the base 302. In this figure, the internal chamber 334 is depicted below the septum 336 that seals the void 316. The housing well 330 may be either integral with or otherwise secured to a housing 332 itself. The depicted embodiment shows an insertion device integral with a medical delivery device (e.g., an infusion device). Other embodiments and applications are contemplated. The housing well 330 defines one or more vertical slots 338, sized and configured to receive the one or more lugs 306 extending from the cannula base 302. The slots 338 are located to ensure alignment of the chamber extension 312 with the channel 340 when the cannula 300 is in the extended position. The channel 340 may be formed within a housing wall or riser 342 or may be a discrete tube secured to the housing 332.

Figure 16:
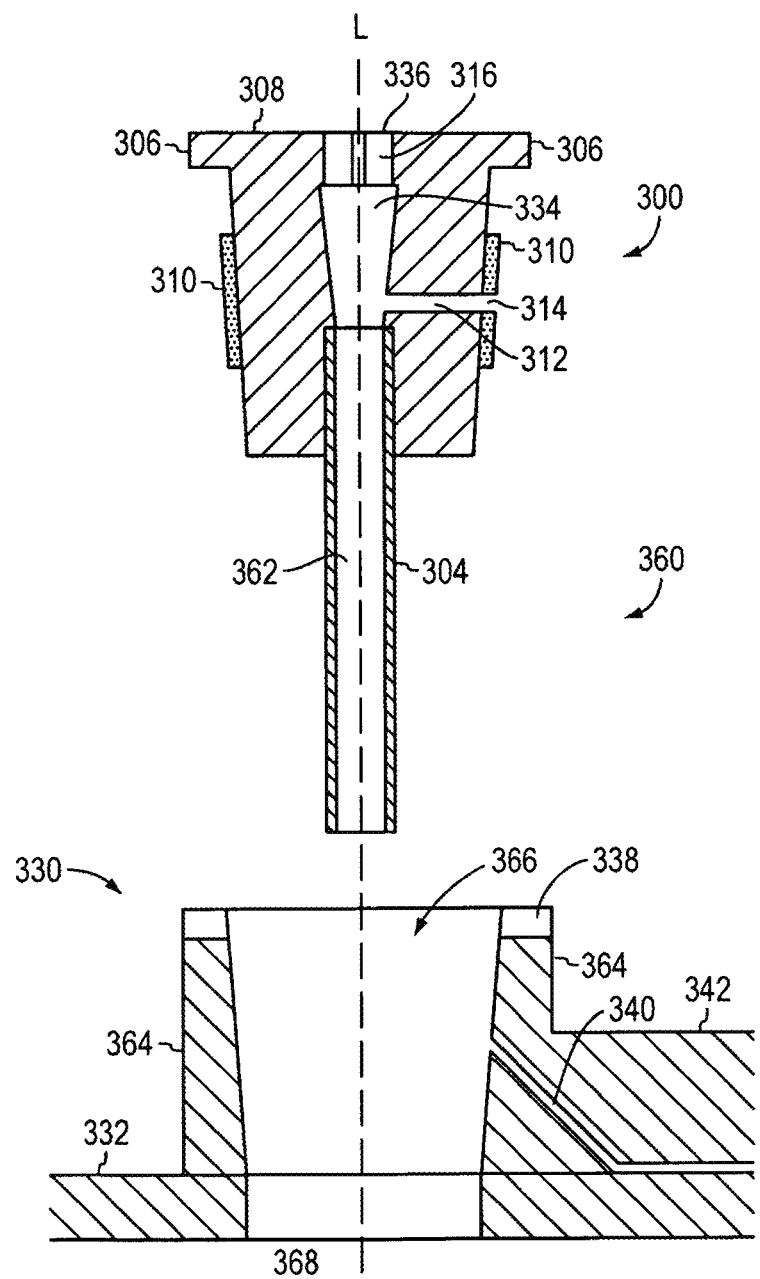
FIG. 16 is a schematic side sectional view of the cannula of FIG. 15A in a retracted position from an associated housing.
Figure 17:
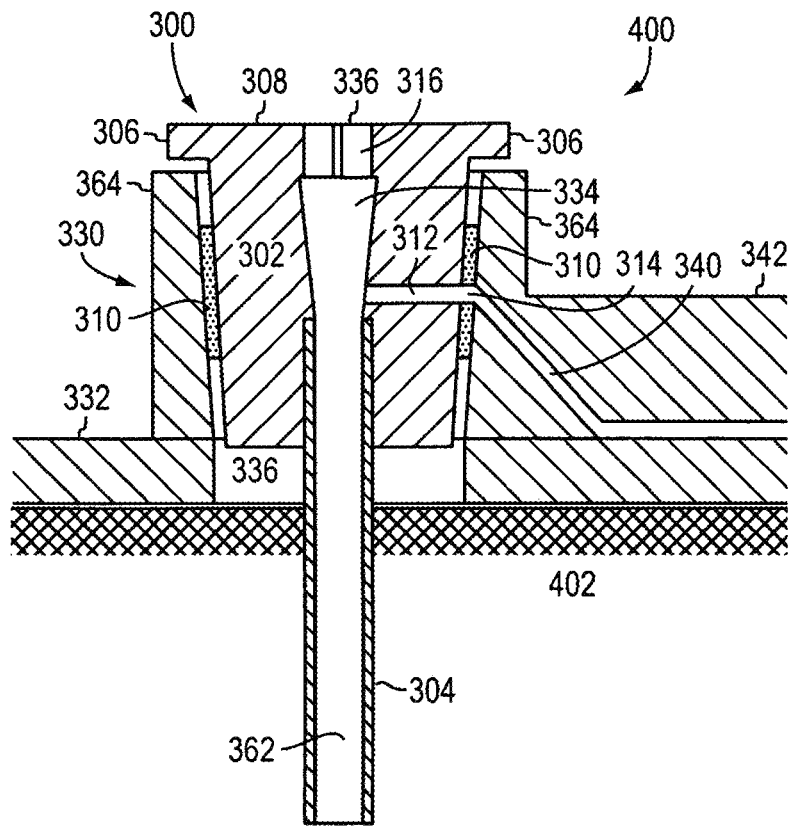
FIG. 17 is a schematic side sectional view of the cannula of FIG. 15A in an extended position.
Figure 18:
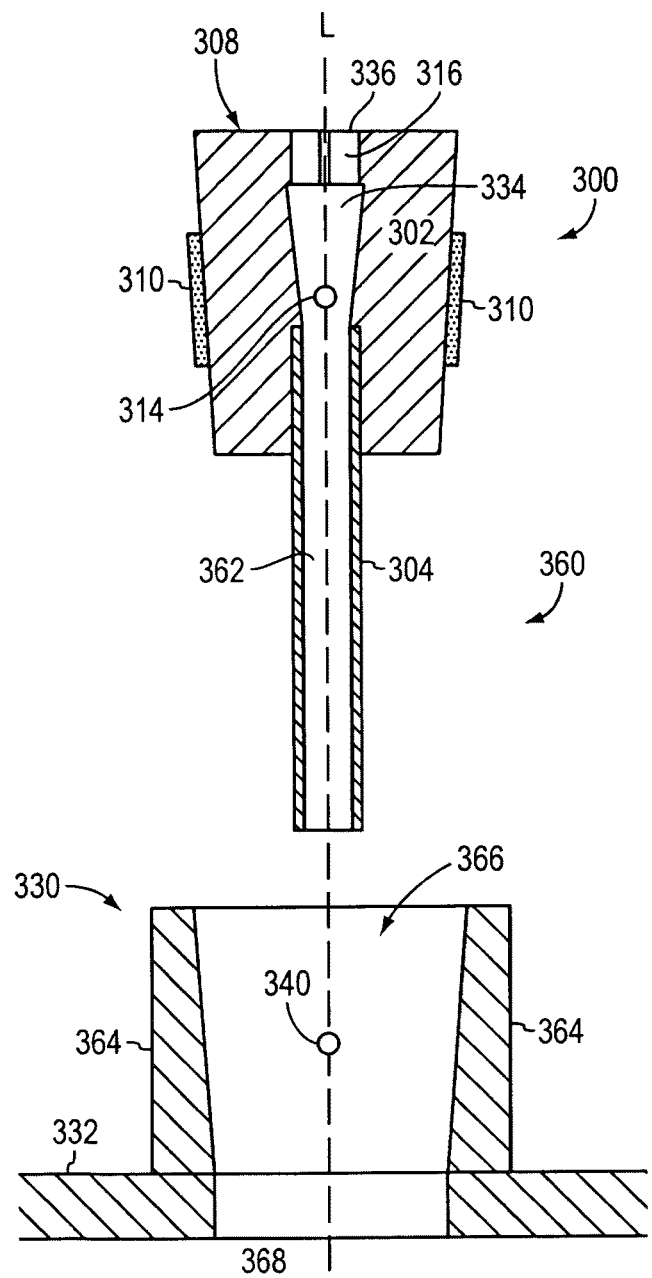
FIG. 18 is a schematic side sectional view of the cannula of FIG. 15A in the retracted position.
Figure 19:
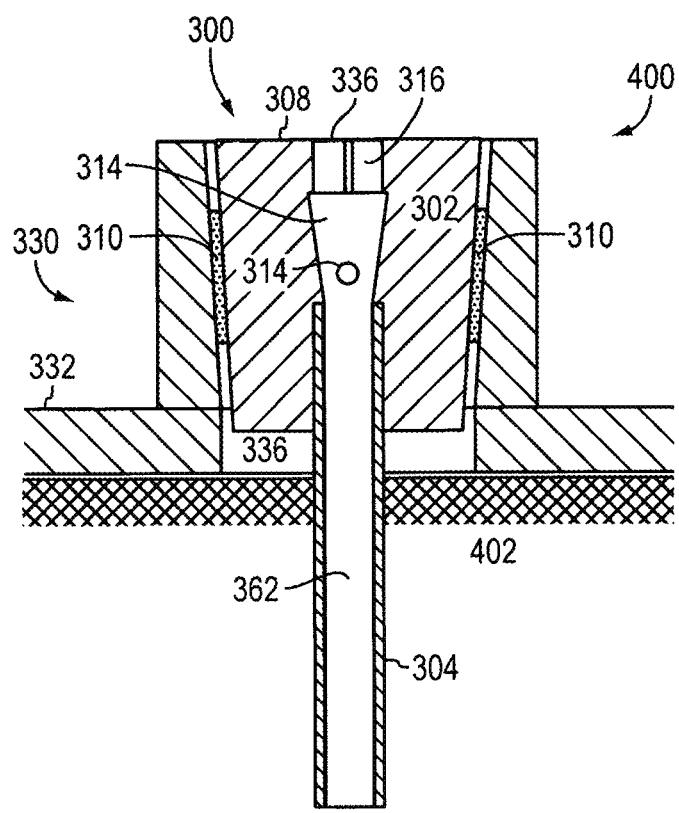
FIG. 19 is another schematic side sectional view of the cannula of FIG. 15A in the extended position.

FIG. 16 is a schematic side section view of the automatically-aligning cannula 300 in a retracted position 360 above the housing well 330. FIG. 18 shows the same configuration, in a section oriented orthogonal to the section depicted in FIG. 16. In FIG. 16, internal chamber 334 is in fluidic communication with the exterior of the base 302 (via the chamber extension 312 and port 314). In turn, a lumen 362 formed within the cannula 304 forms a fluidic path from the chamber 334, out of the device and into a patient, when the cannula 304 is in the extended position (FIGS. 17 and 19). The housing well 330 is formed by an annular wall 364 that, as described above, forms therein a number of slots 338 for mating with the lugs 306. In the depicted embodiment, the housing well 330 is not formed integrally with the housing 332, but as described above, may be so formed in other embodiments. The annular wall 364 defines a tapered frustoconical opening 366 sized to receive the cannula base 302. This opening 366 is in direct fluidic communication with the environment 368 outside of the device housing 332. When the housing 332 is attached to the skin of a patient, the opening 366 will abut the skin. As depicted in FIG. 16, when in the retracted position 360, the channel 340 is in direct fluidic communication with the opening 366 and, consequently, the outside environment 368.

FIG. 17 is a schematic side section view of the automatically-aligning cannula 300 in an extended position 400 within the opening 336 of the housing well 330. FIG. 19 shows the same configuration, in a section oriented orthogonal to the section depicted in FIG. 17. Notably, in the extended position 400, the resilient sheath 310 firmly secures the cannula base 302 within the tapered opening 336 formed within the housing well 330, thus sealing the opening 336. Additionally, the tapered shape of the base 302 and the location of the resilient sheath 310 help ensure alignment of the chamber extension 312 and the channel 340. The embodiment depicted in FIG. 17 depicts the chamber extension 312 and the channel 340 as being approximately the same diameter. This is not required; in fact, it may be advantageous to size the chamber extension 312 larger than the channel 340 to help ensure that those two conduits will be in fluidic communication when the cannula base 302 is in the extended position 400.

In the extended position 400, the cannula 304 extends into a patient 402. While this application refers generally to insertion of the cannula 304 into the skin of a patient for the delivery of insulin, other uses are also contemplated. For example, the insertion device could be used to insert a cannula or catheter into a blood vessel or directly into a body organ. The automatically-aligning feature of the insertion device described herein immediately forms a fluidic connection, by aligning openings in mating surfaces, and serves the same advantages in any number of applications.

FIGS. 20A-20C depict steps associated with one embodiment of inserting a automatically-aligning cannula 502. The figures depict the insertion device 500 in the retracted (FIG. 20A), extended (FIG. 20B), and needle withdrawn (FIG. 20C) positions. In the retracted position (FIG. 20A), automatically-aligning cannula 502 is aligned along an insertion device axis L with housing well 504. Automatically-aligning cannula 502 includes a base 506, a cannula 508, and a needle 510. The needle 510 penetrates a self-sealing septum 512 and passes through first an internal chamber 514 in the base, then through a lumen 516 formed by the cannula 502. The needle end 510a may terminate at or below the bottom of the cannula 508. As mentioned above, the outer diameter of the needle 510 and the inner diameter of the cannula 508 (i.e., the size of the lumen 516) are typically a close sliding fit. Additionally, the base 506 defines a chamber extension 518 through an outer wall 520 of the base 506. The chamber extension 518 defines an chamber extension axis $A_E$, depicted here as being orthogonal to the insertion device axis L. Other orientations of the chamber extension axis $A_E$ are contemplated, including those perpendicular to or parallel with the outer wall 520.

The outer wall 520 is, in certain embodiments, tapered at an angle α relative to a centerline of the cannula 502 and the colinear insertion device axis L. Angle α is also substantially the same as corresponding angle α' of walls 522 in the housing well 504. In general, angles α and α' aid in seating the automatically-aligning cannula 502 within the housing well 504. Channel 524 is located within the wall 522 and defines a channel axis $A_C$ that may be orthogonal to axis L, or orthogonal to the inner edge 526 of wall 522, or otherwise oriented.

To use the insertion device 500, a medical device 528 (for example, an insulin infusion device) containing the insertion device 500 is first placed against the skin 530 of a patient, such that an opening 532 defined at least in part by the housing well 504 is proximate the skin 530. In this orientation, chamber extension 518 is in fluidic communication with the interior of the device 528, as is the lumen 516 and channel 524 (since the opening 532 is located proximate the interior of the device 528, these elements are also in fluidic communication with the opening 524). In the retracted position, both the chamber extension 518 and the lumen 516 are located remotely from the channel 524, or, more specifically, they are not in fluidic communication with the channel 524. In the retracted position, the chamber extension 518, lumen 516, and channel 524 are in fluidic communication only with the interior of the device 528. However, neither the chamber extension 518 nor lumen 516 are in fluidic communication with the channel 524. Fluidic communication is not possible between the channel 524 and lumen 516 (via the chamber extension 518 and internal chamber 514) until the cannula base 506 is in the extended position. To reach this position, a force $F_{NB}$ is applied to either or both of the needle 510 and cannula base 506 to drive both into the housing well 504.

The extended position of the insertion device 500 is depicted in FIG. 20B. In this position, cannula 508 and needle end 510 both penetrate the skin 530 of the patient. Additionally, when in the extended position, channel axis $A_C$ and chamber extension axis $A_E$ are aligned along a common axis A. While FIG. 20B depicts actual alignment of axes $A_C$ and $A_E$, alignment of axes is not required. In other embodiments, for example, where one or both of the axis are not orthogonal to the device axis L (see FIGS. 16-17, for example), intersection or close proximity of the axes sufficient to ensure fluidic communication from the channel 524 to the skin 530 of the patient is acceptable. In other embodiments, sufficient overlapping of areas of the channels would be sufficient to ensure fluidic communication. Although depicted schematically in the figures with significant clearance to facilitate depiction, needle 510 is a close sliding fit within the lumen 516 of the cannula 508. Accordingly, to allow unrestricted fluidic communication from the channel 524 to the patient, needle 510 is removed from the cannula 508. To do so, a force $F_N$ is applied to the needle 510 to withdraw it from the cannula 508. The various embodiments of the insertion devices described hereinabove may be used to perform this function. The friction fit between the cannula base 502 and the housing well 504 retains the cannula base 502 in place and seals the fluidic communication path.

The withdrawn position of the insertion device 500 is depicted in FIG. 20C. In this position, the needle 510 has been withdrawn from the cannula base 502, while the base 502 itself remains in place within the housing well 504. Upon withdrawal, the self-sealing septum 512 closes behind the needle 510 to ensure a fluid tight seal. Once the needle 510 is withdrawn, there is fluidic communication from the device 528 to the patient, via the channel 524, chamber extension 518, internal chamber 514, and the lumen 516. In an alternative embodiment, the needle is withdrawn completely from the patient, but need not be withdrawn completely from the cannula base. Since the needle is closely fit within the lumen of the cannula, the flow of insulin may still be prevented by the position of the needle. In that regard, a hollow needle having an opening defined in the sidewall thereof may allow for the passage of insulin into the hollow needle. The insulin then passes through the cannula lumen and into the patient.

The embodiments of the automatically-aligning cannula system depicted in FIGS. 14-20C have distinct advantages over known cannula insertion systems that utilize a hollow needle or tube to form a fluidic connection between a fluid flow passage and a lumen of a cannula. In such systems, the hollow needle penetrates a septum that seals the fluid flow passage prior to use (in this case, the fluid flow passage is always isolated from the interior of the device by the septum). In contrast, the disclosed automatically-aligning cannula system does not require a needle and septum to create a fluid seal. In that regard, the disclosed invention presents a more elegant solution that reduces manufacturing costs and ensures proper operation. The surface-to-surface sealing configuration of the present invention reduces manufacturing costs by eliminating the need for an additional needle, septum, or complex injection molded parts to incorporate those elements. Additionally, assembly costs are similarly reduced, as the needle and septum need not be incorporated into the device.

Instead of using a septum and a penetrating needle to ensure a fluidic connection, the disclosed cannula system aligns two curved surfaces, namely, the curved inner wall of the housing well and the outer surface of the frustoconical cannula base. The resilient sheath helps to seal any imperfections formed during the manufacturing process, thus improving the friction fit of the cannula base within the housing well. Additionally, the sheath aids in sealing the fluidic connection between the chamber extension and the channel, thus preventing leakage of fluid. By eliminating the needle and septum, both the chamber extension and the channel are in fluidic communication (i.e., not isolated) from the interior of the device when the cannula base is in the retracted position. In the extended position, the chamber extension and channel are placed in fluidic communication by alignment, while the connection is sealed by the sheath.

The various components utilized in the device described herein may be metal, glass, and/or any type of polymer suitable for sterilization and useful for delivering insulin or other medicaments subcutaneously. Polyurethane, polypropylene, PVC, PVDC, EVA, and others, are contemplated for use. More specifically, medical-grade plastics may be utilized for the cannula itself, as well as other components that contact or otherwise penetrate the body of the patient. Needles and springs made from medical-grade stainless steel are also desirable, to prevent failure associated with use.

While there have been described herein what are to be considered exemplary and preferred embodiments of the present invention, other modifications of the invention will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the invention. Accordingly, what is desired to be secured by Letters Patent is the invention as defined and differentiated in the following claims, and all equivalents.

What is claimed is:

1. A cannula insertion device comprising:
   a housing defining a frustoconical opening for receiving therethrough a cannula, a slot for receiving a lug of the cannula, and further defining a channel;
   a cannula forming a lumen and comprising a lug adapted to mate with the slot, a frustoconical base adapted to mate with the housing frustoconical opening, the base defining an internal chamber in fluidic communication with the lumen, wherein the cannula is adapted for self-aligning sliding movement within the housing from a retracted position to an extended position; and
   a needle disposed in the lumen when the cannula is in the retracted position, wherein:
      when the cannula is in the retracted position, the lumen is located remotely from the channel and the channel is in fluidic communication with the housing frustoconical opening which is in fluidic communication with an outside environment; and
      when the cannula is in the extended position, the lumen is in fluidic communication with the channel due to mating of the lug with the slot without having to separately connect a tube thereto, and the channel is no longer in fluidic communication with the housing frustoconical opening.

2. The cannula insertion device of claim 1, wherein the base further defines a chamber extension in fluidic communication with the internal chamber.

3. The cannula insertion device of claim 2, wherein when the cannula is in the extended position, the chamber extension is aligned with the channel.

4. The cannula insertion device of claim 2, wherein a wall of the base defines the chamber extension.

5. The cannula insertion device of claim 4, wherein the base includes a resilient sheath, the sheath defining a port substantially aligned with the chamber extension.

6. The cannula insertion device of claim 5, wherein when the cannula is in the extended position, the port is aligned with the channel.

7. The cannula insertion device of claim 5, wherein when the cannula is in the extended position, the sheath seals the opening.

8. The cannula insertion device of claim 1, further comprising a plunger for driving the cannula from the retracted position to the extended position.

9. The cannula insertion device of claim 1, wherein the needle is adapted to be automatically withdrawn from the lumen when the cannula is in the extended position.

10. The cannula insertion device of claim 1, wherein the cannula is adapted to be automatically disconnected from the plunger when the cannula is in the extended position.

11. A method of inserting a cannula, the method comprising the steps of:
   providing a housing defining a frustoconical opening for receiving therethrough a cannula, a slot for receiving a lug of the cannula, and further defining a channel;
   providing a cannula forming a lumen with a needle disposed therein, the cannula comprising a lug adapted to mate with the slot, a frustoconical base adapted to mate with the housing frustoconical opening, the base defining an internal chamber in fluidic communication with the lumen, wherein the cannula is adapted for self-aligning sliding movement within the housing from a retracted position to an extended position; and
   extending the cannula from the retracted position, in which the lumen is located remotely from the channel and the channel is in fluidic communication with the housing frustoconical opening which is in fluidic communication with an outside environment, to the extended position, in which the lumen is in fluidic communication with the channel due to mating of the lug with the slot without having to separately connect a tube thereto, and the channel is no longer in fluidic communication with the housing frustoconical opening.

12. The method of claim 11, further comprising the step of piercing a skin of a patient with the needle and the cannula as the cannula moves from the retracted position to the extended position.

13. The method of claim 12, further comprising the step of withdrawing the needle from the lumen automatically when the cannula is in the extended position.

14. The method of claim 12, wherein a plunger extends the cannula from the retracted position to the extended position, the plunger in contact with the needle.

15. The method of claim 14, further comprising the step of disconnecting the cannula from the plunger when the cannula is in the extended position.

16. The method of claim 11, further comprising the step of sealing the opening with the cannula when the cannula is in the extended position.

* * * * *